United States Patent
Wang et al.

(10) Patent No.: US 7,939,338 B2
(45) Date of Patent: May 10, 2011

(54) MAGNETIC SENSOR ARRAY HAVING AN ANALOG FREQUENCY-DIVISION MULTIPLEXED OUTPUT

(75) Inventors: Shan X. Wang, Portola Valley, CA (US); Shu-Jen Han, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1668 days.

(21) Appl. No.: 11/128,105

(22) Filed: May 11, 2005

(65) Prior Publication Data

US 2005/0258821 A1     Nov. 24, 2005

Related U.S. Application Data

(60) Provisional application No. 60/570,672, filed on May 12, 2004.

(51) Int. Cl.
*G01R 33/00* (2006.01)
(52) U.S. Cl. ...... 436/149; 436/56; 422/68.1; 422/82.01; 210/222
(58) Field of Classification Search ............ 436/56, 436/149, 526; 422/68.1, 82.01; 210/222
See application file for complete search history.

(56) References Cited

U.S. PATENT DOCUMENTS

| | | | | |
|---|---|---|---|---|
| 3,941,982 A | | 3/1976 | Knollenberg et al. ......... 235/92 |
| 5,272,476 A | | 12/1993 | McArthur et al. ....... 340/870.13 |
| 5,747,997 A | * | 5/1998 | Dahlberg et al. ............. 324/252 |
| 5,981,297 A | * | 11/1999 | Baselt ............................ 436/514 |
| 6,535,822 B2 | | 3/2003 | Mansky et al. .................. 702/21 |
| 6,627,154 B1 | * | 9/2003 | Goodman et al. ......... 422/82.01 |
| 6,765,699 B1 | | 7/2004 | Spears .......................... 358/482 |
| 6,785,528 B2 | * | 8/2004 | Carpineto .................... 455/323 |
| 7,349,466 B2 | * | 3/2008 | Coker et al. .................. 375/222 |
| 2003/0222702 A1 | * | 12/2003 | Bjork et al. ................... 327/355 |
| 2004/0033627 A1 | | 2/2004 | Aytur et al. .................... 436/526 |
| 2004/0120185 A1 | | 6/2004 | Kang et al. ..................... 365/158 |

* cited by examiner

*Primary Examiner* — Robert J Hill, Jr.
*Assistant Examiner* — Dwan A Gerido
(74) *Attorney, Agent, or Firm* — Lumen Patent Firm

(57) ABSTRACT

A magnetic sensor array including magnetoresistive sensor elements having outputs combined by frequency division multiplexing (FDM) is provided. Each sensor element provides an input to a mixer which provides a distinct frequency shift. Preferably, time division multiplexing is also used to combine sensor element outputs. Each sensor element is typically in proximity to a corresponding sample. The sensor elements are preferably subarrays having row and column addressable sensor element pixels. This arrangement provides multiple sensor pixels for each sample under test. Multiplexing of sensor element outputs advantageously reduces readout time. A modulated external magnetic field is preferably applied during operation, to reduce the effect of 1/f noise on the sensor element signals. The effect of electromagnetic interference (EMI) induced by the magnetic field on sensor element signals is advantageously reduced by the mixing required for FDM.

23 Claims, 6 Drawing Sheets

MAGNETIC SENSOR ARRAY HAVING AN ANALOG FREQUENCY-DIVISION MULTIPLEXED OUTPUT

CROSS REFERENCE TO RELATED APPLICATIONS

This application claims the benefit of U.S. provisional application 60/570,672 filed on May 12, 2004, entitled "Low Noise and High Speed Magnetic Microarray IC Chip Designs", and hereby incorporated by reference in its entirety.

GOVERNMENT SPONSORSHIP

This invention was made with support from DARPA under grant number N00014-02-1-0807. The US Government has certain rights in this invention.

FIELD OF THE INVENTION

This invention relates to sensing of magnetically tagged substances.

BACKGROUND

Assay techniques generally relate to determination of the composition of a sample (e.g., whether or not a component of interest is in the sample, concentration of the component, etc.). Assays are commonly employed in biological and chemical applications. For example, molecular recognition often provides specificity and selectivity for important biological processes. Such molecular recognition is exploited in assay techniques such as those based on DNA hybridization microarrays and protein arrays.

Present day assay techniques are often implemented using an array of sensors, each sensor corresponding to a separate assay sample. The use of such a sensor array allows for many different assays to be carried out in parallel, and the resulting improvement in throughput is typically of great practical significance.

Accordingly, various technological approaches for providing suitable sensor arrays have been developed in the art. One such approach is magnetic tagging, as considered in U.S. Pat. No. 5,981,297 and U.S. 2004/0120185. Magnetic biosensors are under active development, and may soon rival established biological detection methods involving surface-bond fluorescent tags. For example, suppose it is desired to sense the presence of a particular DNA oligomer type X in a liquid sample. This can be accomplished via the following steps: 1) tag the oligomers in the sample with magnetic tags; 2) attach a probe oligomer to a sensor surface, where the probe oligomer is complementary to type X; 3) sense the presence or absence of a magnetic tag at the sensor. Since only oligomers of type X can hybridize to the probe at the sensor surface, the presence or absence of type X oligomers can be determined by sensing the tags with a magnetic sensor.

Since it is often desirable to perform assays on a large number of samples, methods for rapidly reading out results from a sensor array have been considered. For example, U.S. Pat. No. 3,941,982, U.S. Pat. No. 5,272,476, U.S. Pat. No. 6,535,822, U.S. Pat. No. 6,765,699 and U.S. 2004/0033627 consider sensor array readout in various contexts. Some of these references relate to time division multiplexing, where the outputs from several sensor elements are combined onto a single array output by time division multiplexing. For example, the common situation where sensor array elements are addressed sequentially by rows and columns is an instance of time division multiplexing.

However, certain problems relating to sensor arrays are not addressed by these methods. In particular, it is important to consider the time it takes a tagged part of the sample (i.e., a tagged component) to bind to the sensor surface. Typically, the sensor surface is sensitized with a complimentary oligomer probe. For example, consider a sensor element in proximity to a oligomer probe spot having a diameter of 200 µm. Such an oligomer probe spot is often deposited robotically and includes many identical copies of the oligomer. If the sensitized sensor element is comparable in size to the oligomer spot, then the tagged component will bond to the sensor surface relatively quickly. Conversely, if the sensitized sensor element is much smaller than the DNA spot, then the tagged component will bond to the sensor surface relatively slowly. Since the tagged component diffuses randomly above the oligomer probe spot, it will take longer to encounter a small sensor than a large sensor. However, a large sensor tends to be less sensitive than a small sensor. Therefore, conventional assay arrays typically require a design that balances a desire for high sensitivity (i.e., small sensors) with low binding delay (i.e. large sensors).

Modification of prior art sensor arrays to address this problem (e.g., by providing several sensor element pixels per oligomer spot in the preceding example) is not straightforward. For example, such provision of additional sensor element pixels can significantly and undesirably increase readout time. Accordingly, it would be an advance in the art to provide a sensor array for magnetically tagged samples providing rapid and sensitive detection of tagged components.

SUMMARY

The present invention provides a magnetic sensor array including magnetoresistive sensor elements having outputs combined by frequency division multiplexing (FDM). Each sensor element provides an input to a mixer which provides a distinct frequency shift. Preferably, time division multiplexing is also used to combine sensor element outputs. Each sensor element is typically in proximity to a corresponding sample. The sensor elements are preferably subarrays having row and column addressable sensor element pixels. This arrangement provides multiple sensor pixels for each sample under test. Multiplexing of sensor element outputs advantageously reduces readout time. A modulated external magnetic field is preferably applied during operation, to reduce the effect of 1/f noise on the sensor element signals. The effect of electromagnetic interference (EMI) induced by the magnetic field on sensor element signals is advantageously reduced by the mixing required for FDM.

BRIEF DESCRIPTION OF THE DRAWINGS

FIG. 3b shows a calculated noise spectrum of the sensor configuration of FIG. 3a.

FIG. 4b shows a calculated noise spectrum of the sensor configuration of FIG. 4a.

DETAILED DESCRIPTION

Figure 1:
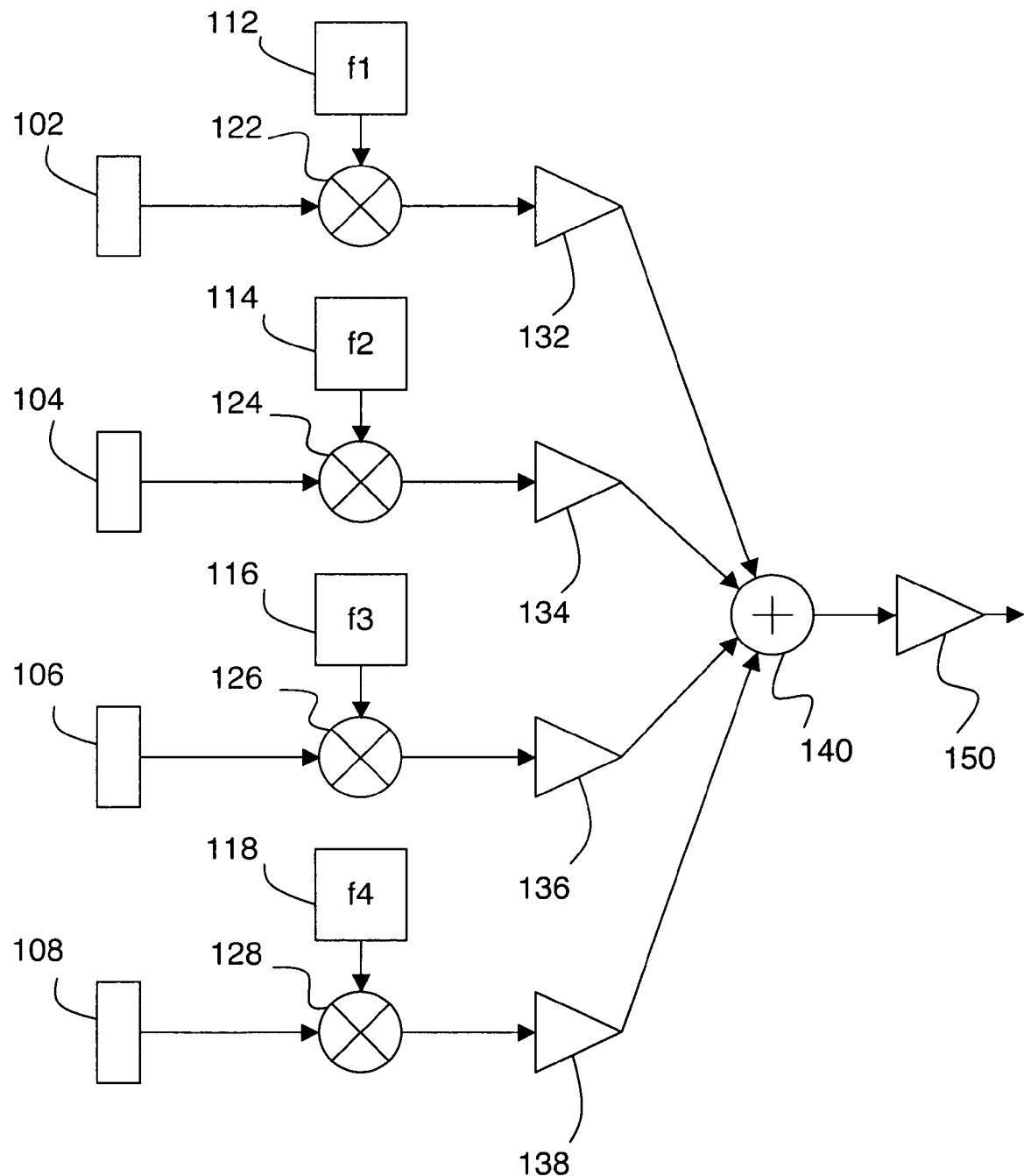
FIG. 1 is a block diagram of an embodiment of the invention.

FIG. 1 is a block diagram of an embodiment of the invention. A magnetoresistive (MR) sensor element 102 provides a sensor element signal to a mixer 122. Mixer 122 also receives a signal having frequency f1 from a source 112. Mixer 122 provides a frequency shifted sensor element signal to an output summing junction 140. More specifically, the frequency shifted sensor element signal differs in frequency from the sensor element signal by +/−f1. Sensor element 102 and mixer 122 form a sensor subassembly. This sensor subassembly preferably includes amplifier 132. Amplifier 132 receives the frequency shifted sensor signal and provides an amplified frequency shifted signal to output summing junction 140. Optionally, further on-chip processing is performed by processor 150. For example, processor 150 can include a programmable gain amplifier to improve the dynamic range of the overall system.

Embodiments of the invention include two or more such sensor subassemblies. For example, FIG. 1 shows four subassemblies, and the invention can be practiced with any number of subassemblies. Each sensor subassembly has a distinct frequency shift. Thus no two of f1, f2, f3, and f4, provided by sources 112, 114, 116, and 118 respectively are equal. Output summing junction 140 provides a combined output that is proportional to a sum of all of the frequency shifted sensor element signals (one from each sensor subassembly). Therefore the arrangement of FIG. 1 shows analog frequency division multiplexing (FDM) of sensor element outputs. Such FDM is a key aspect of the invention, and various advantages follow from this frequency division multiplexing as indicated in the following description.

The present invention is suitable for use with any magnetically tagged sample. Magnetically tagged samples include, but are not limited to, biological samples and chemical samples. Exemplary biological samples suitable for use with the invention include oligomer samples, DNA samples, RNA samples, proteins, peptides, antibodies, antigens, lipids, and viruses. Exemplary chemical samples suitable for use with the invention include polymers, toxins, pharmaceutical compounds, biohazardous compounds and explosive compounds.

MR sensor elements 102, 104, 106, and 108 can include any magnetoresistive device or devices providing an electrical resistance that depends on magnetic field. Such devices include, but are not limited to, spin valves and magnetic tunnel junctions. These MR sensor elements can be single sensor elements, or can be subarrays including several sensor element pixels. Subarrays are usually preferable, and accordingly the following description includes several examples of subarray embodiments. In some embodiments, the MR sensor elements include a molecular probe coating for binding to a specific tagged molecular species in the sample.

Mixers 122, 124, 126, and 128 are preferably double-balanced, passive mixers fabricated with CMOS technology. Although these mixers can be operated at any frequency, a frequency range from about 15 kHz to about 20 kHz has been found suitable in practice. The mixer output frequency should be high enough to allow for filtering to remove low frequency noise (e.g., electromagnetic interference, 1/f noise, etc.). The mixer output frequency should also be sufficiently low that the following circuitry is not unduly complicated by high frequency design considerations. In any particular case, it is within the skill of an art worker to select an appropriate mixer output frequency according to these principles.

Figure 8:
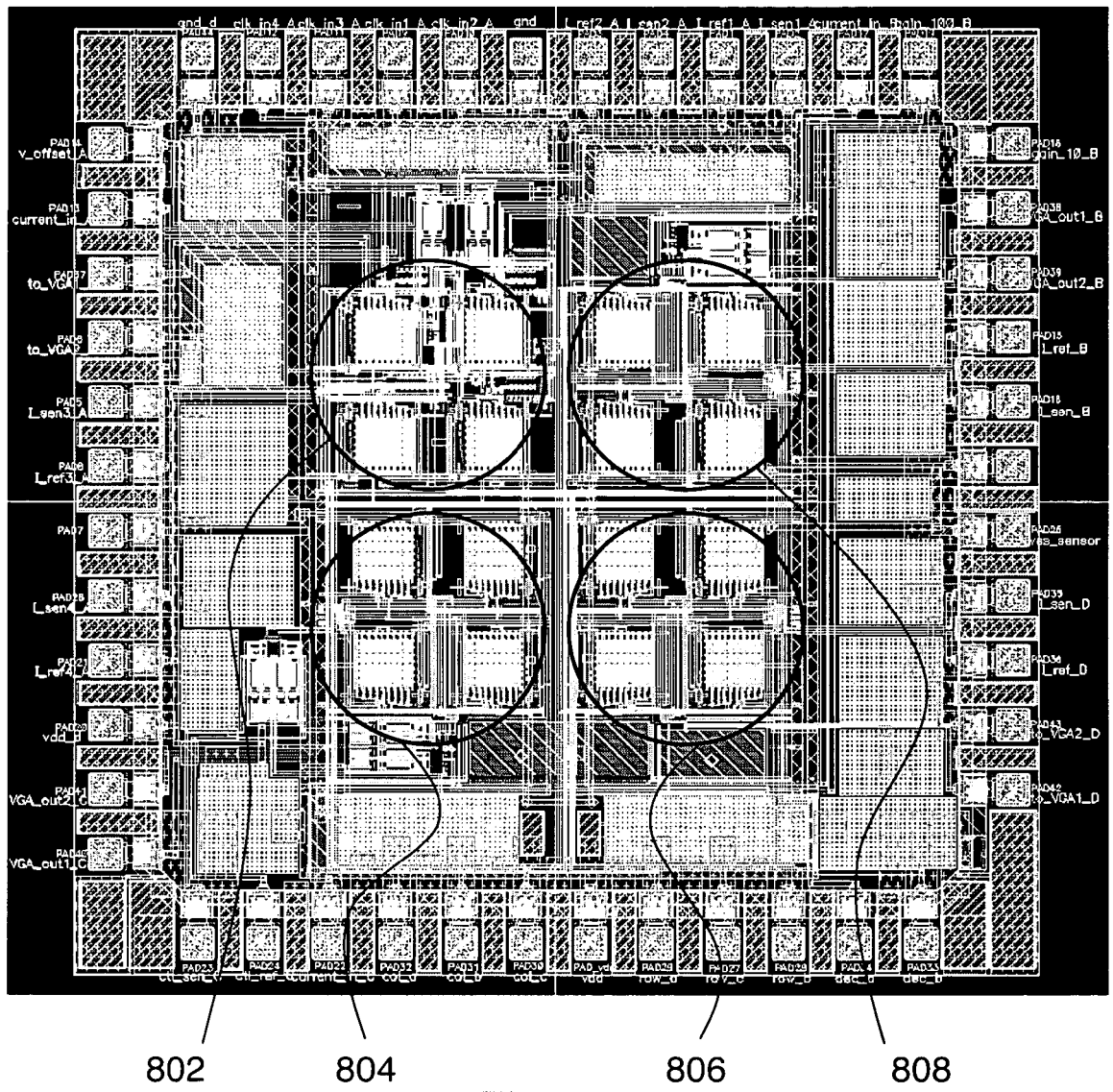
FIG. 8 shows a chip layout of an embodiment of the invention.

Amplifiers 132, 134, 136, and 138, are preferably linear low noise amplifiers (LNAs), since the sensor signals are analog signals. The use of BiCMOS technology is preferred in the LNA to reduce noise, although CMOS technology is also applicable to the LNA. The LNAs used in the example of FIG. 8 are BiCMOS circuits having a gain of about 10 and an input referred noise of less than 10 nV/√Hz over the frequency range of interest (15-20 kHz in this case).

Figure 2:
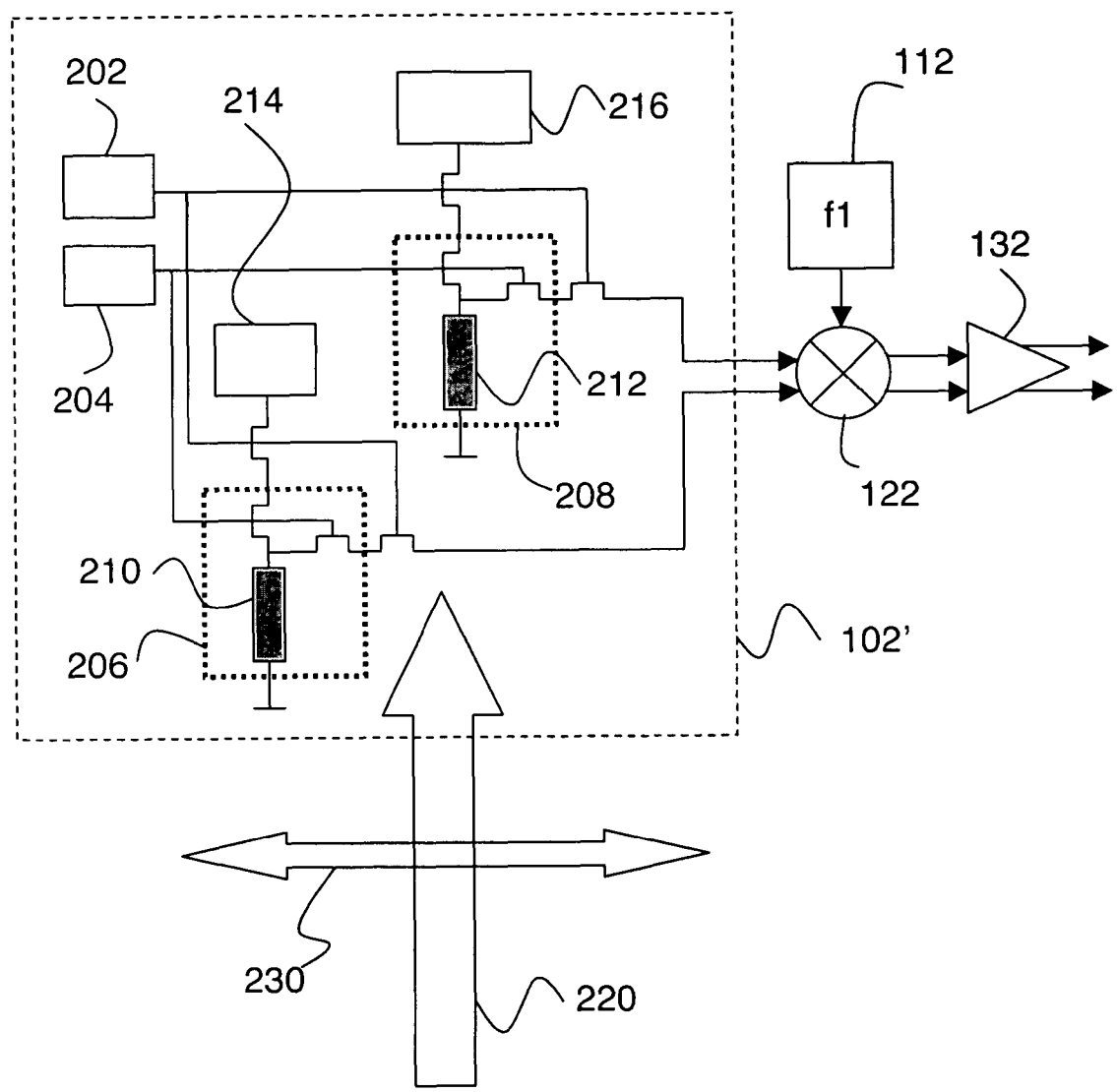
FIG. 2 shows details relating to an MR sensor element according to an embodiment of the invention.

FIG. 2 shows further detail relating to an MR sensor element according to an embodiment of the invention. Within an MR sensor element pixel 102' (large dashed rectangle 102' on FIG. 2), there is an active MR device 210 and a reference MR device 212. MR devices 210 and 212 are included within sensor cells 206 and 208 respectively. Each sensor cell includes two transistors in addition to the MR device. Further details relating to sensor cells are given in connection with FIGS. 3a-b and 4a-b. Sensor cells 206 and 208 provide a differential input to mixer 122. Reference device 212 is disposed at a location away from the sample under test, while active device 210 is disposed in proximity to the sample under test. Thus presence of a magnetically tagged sample component affects active device 210 but does not affect reference device 212. Formation of a differential input to mixer 122 beneficially cancels out background signals that are independent of the sample.

Sensor cells 206 and 208 are driven by sources 214 and 216 respectively. Sources 214 and 216 are preferably voltage controlled current sources, providing a current to devices 210 and 212 respectively. Such current sources are preferably adjusted during a calibration procedure to remove offsets due to variable device characteristics (particularly of MR devices 210 and 212). More specifically, the sources are adjusted to provide no differential signal to mixer 122 when a magnetically tagged sample is not present at sensor 210. The results of this calibration can be stored digitally to reduce or eliminate the need for recalibration over time. Offset cancellation is especially important in view of the large variations (e.g., >5%) typically seen in MR device parameters.

Pixel 102' also includes a row decoder 202 and a column decoder 204. In this embodiment, MR sensor element 102 of FIG. 1 is a subarray of sensor element pixels, each having the structure of pixel 102' on FIG. 2. Thus the setting of the row and column decoders determine which pixel of the subarray is effectively connected to mixer 122. In practice, the row and column decoder settings will be scanned to provide a sequential readout of the signals from the various pixels of the subarray. Methods for providing such row and column addressing are well known in the art, (e.g., in connection with semiconductor memory circuits), and can be adapted to embodiments of the invention. In such adaptation, it is important to note that the present invention relates to analog signals, as opposed to digital signals. Accordingly, it is preferred to design for low noise and linearity of the sensor output.

In operation, it is usually preferred to apply an external magnetic field (220 and 230) to the MR sensors. The applied external field typically has a static component 220 and a modulated component 230. The static and modulated magnetic field components can have vector directions which are similar or different. The external field can be modulated at a frequency $f_B$, which will result in the outputs from sensor cells 206 and 208 also being modulated at $f_B$. Application of static magnetic field 220 can increase the linearity and stability of MR devices, since provision of a magnetic bias field removes magnetic domain boundaries. Magnetic domain boundaries are undesirable, since they lead to hysteresis and increased noise (e.g., Barkhausen noise).

Application of a modulated magnetic field provides "double modulation", since the signal of interest from a tagged sample component is first frequency shifted to $f_B$ by the field modulation, and secondly shifted to $f_B+f_{mixer}$ (or to $f_B-f_{mixer}$) by the mixer. This preferred frequency plan of the invention provides several advantages. First, signal to noise ratio is improved, since the effect of 1/f noise is significantly decreased. Magnetic sensors, such as spin valves, frequently have strong 1/f noise. Second, frequency division multiplexing provides a parallel readout capability. Third, the use of mixers to shift signal frequencies away from the field frequency $f_B$ allows the use of filters to suppress electromagnetic interference (EMI) at $f_B$. Note that significant EMI can be expected in an electrical circuit exposed to a modulated magnetic field. Double modulation can be provided in other ways. For example, the MR sensor elements can be driven by an electrical signal modulated at a frequency $f_A$. The resulting output signals will also be modulated at $f_A$. Thus far, it has been found preferable to provide double modulation by modulating the magnetic field.

Figure 3A:
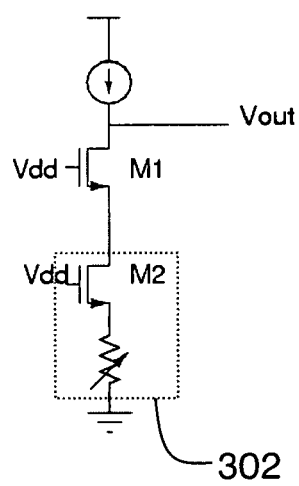
FIG. 3a shows a first sensor configuration suitable for use with the invention.

FIG. 3a shows a first sensor configuration suitable for use with the invention. In the preceding description, sensor cells 206 and 208 included two transistors and one MR device. The advantages of this configuration can be appreciated by comparison to the simpler sensor element cell 302 of FIG. 3a. Since cell 302 includes one transistor and one spin valve (i.e., the variable resistor), this configuration is abbreviated 1T1SV. Here M1 and M2 are operated in the deep-triode region. However, several problems may arise with the 1T1SV configuration. First, M1 and M2 are in a common-source configuration which can undesirably increase noise. Second, since M1 and M2 behave as variable resistors, their AC responses (due to AC voltages at the source terminals) will be coupled with the desired signals from the MR device. Also, M1 and M2 can introduce undesirable nonlinearity.

Figure 3B:
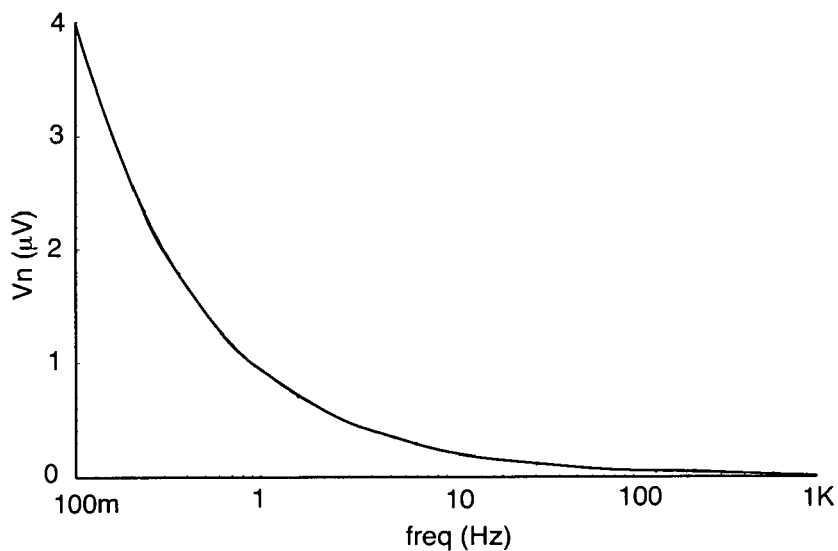
Figure 4A:
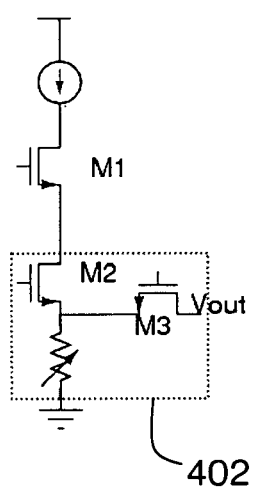
FIG. 4a shows a second sensor configuration suitable for use with the invention.
Figure 4B:
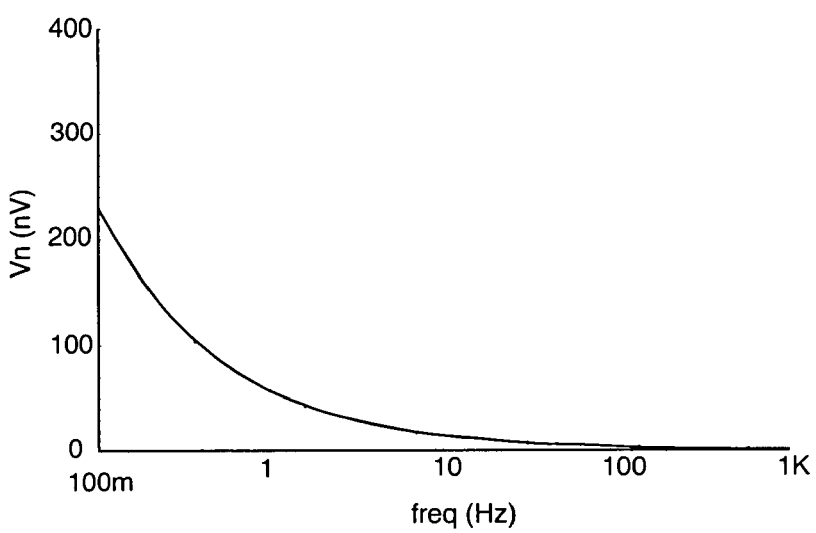

FIG. 4a shows a second sensor configuration suitable for use with the invention. Sensor cell 402 of FIG. 4a is a 2T1SV configuration, like the configuration of FIG. 2. Here M3 has a source follower relation to M2, which reduces noise. FIGS. 3b and 4b show calculated noise spectra (V/√Hz) of the 1T1SV and the 2T1SV sensor cells respectively, demonstrating reduced noise for the 2T1SV cell compared to the 1T1SV cell. The noise of the 2T1SV cell is primarily from the current source. The sensor configuration of FIG. 4a preferably drives a capacitive load, in order to reduce the noise contributed by M3. A preferred method for providing such a capacitive load is for each LNA (e.g., 132 on FIG. 1) to provide a capacitive input load, and for the mixers (e.g., 122 on FIG. 1) to provide a capacitive input load when driving a capacitive load. Mixers and LNAs having such properties are well known in the art.

Figure 5A:
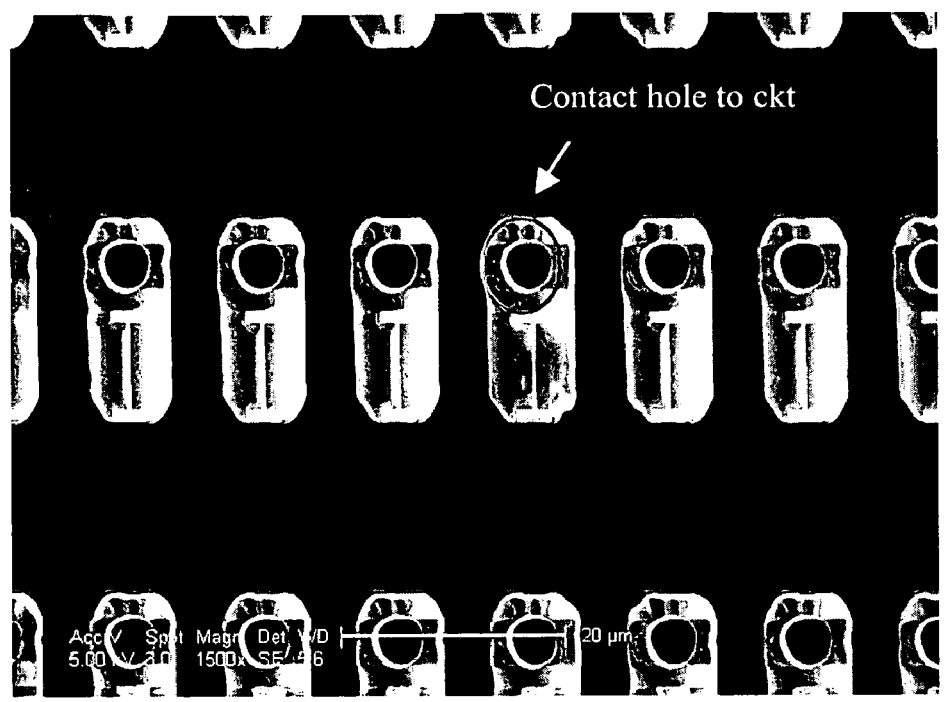
FIGS. 5a-b show SEM images of sensors suitable for use with the invention.
Figure 5B:
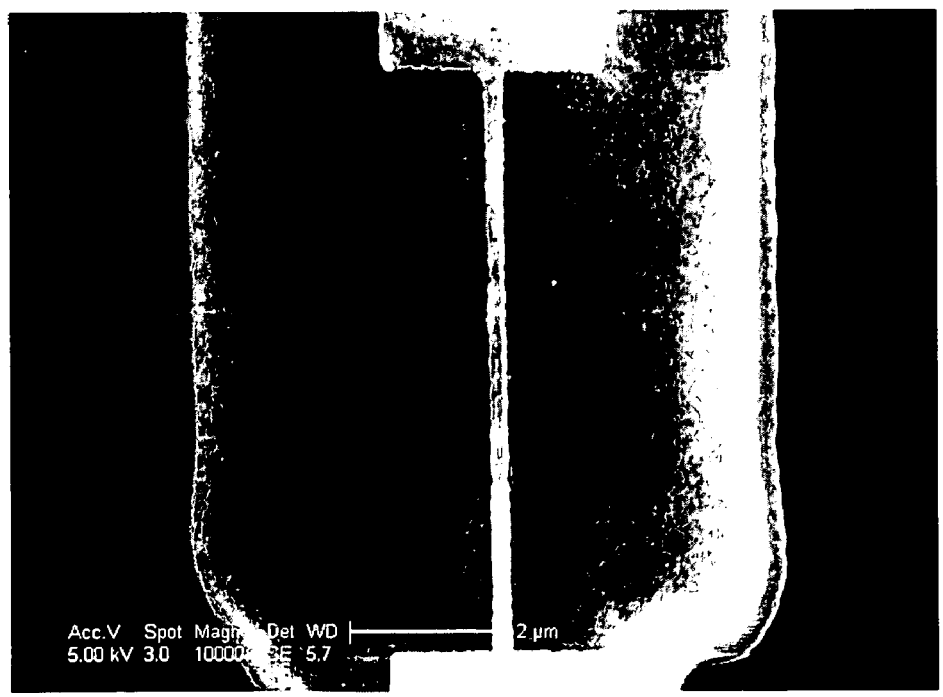

FIGS. 5a-b show SEM images of sensors suitable for use with the invention. The sensors of this example are spin valve sensors. These sensors can be fabricated by physical vapor deposition and can be patterned with photolithography or electron beam lithography (EBL). In this example, the sensors are 10 μm in length and 300 nm in width. Each sensor has one terminal that connects individually to the circuit underneath via a contact hole and another terminal that is electrically connected to a common analog ground.

Figure 6:
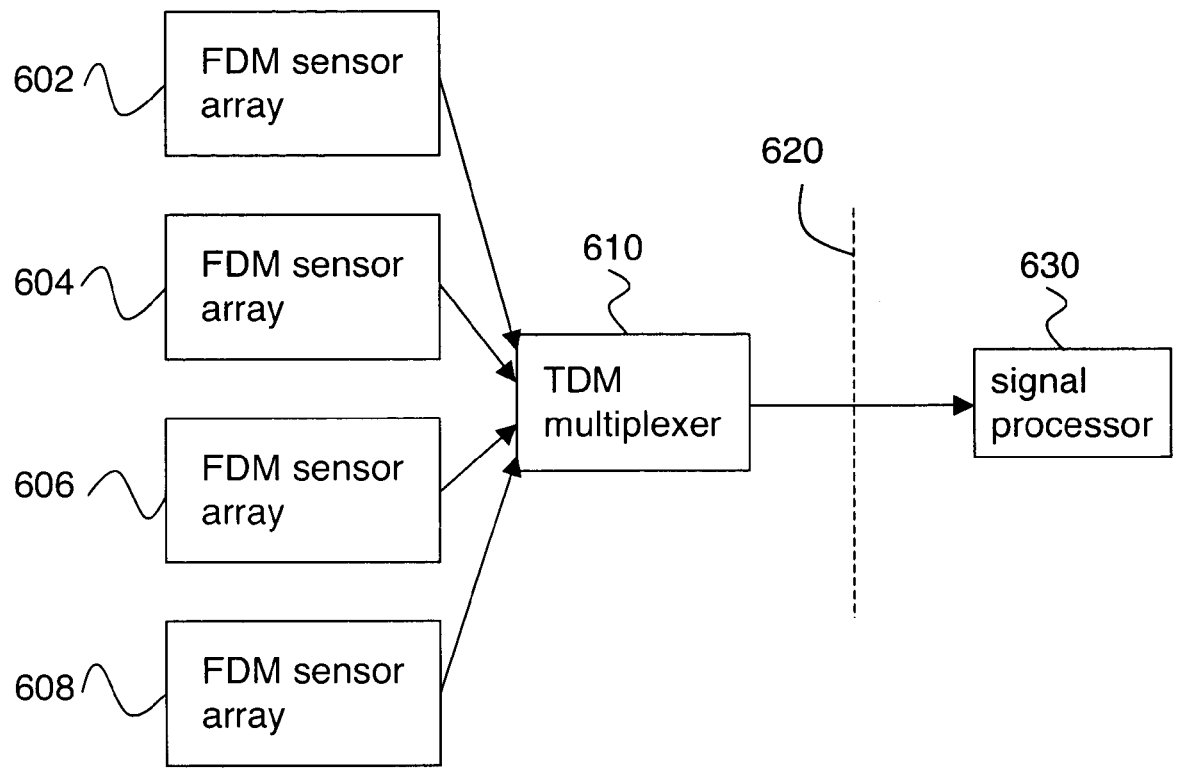
FIG. 6 is a block diagram of an alternate embodiment of the invention.

FIG. 6 is a block diagram of an alternate embodiment of the invention. In the embodiment of FIG. 6, FDM sensor arrays 602, 604, 606, and 608 provide inputs to a multiplexer 610 which provides a multiplexer output signal. The multiplexer output signal is related to the input signal by time division multiplexing (TDM). TDM is well known in the art. The multiplexer output signal can be received by a signal processor 630. Here, FDM sensor arrays such as 602 are understood to be sensor arrays such as shown in FIG. 1. Thus the embodiment of FIG. 6 shows time division multiplexing of several FDM sensor arrays according to the invention. In preferred embodiments, the FDM sensor arrays and the TDM multiplexer are all included in on-chip circuitry (e.g., monolithically integrated), while the signal processor is an off-chip device, component and/or system. This preferred division between on-chip and off-chip functions is schematically indicated by line 620.

Signal processor 630 can extract sensor information in any convenient manner. For example, phase-sensitive detection can be employed to measure the amplitude of tones within the multiplexer output signal at specific frequencies (e.g., at $f_B+f1$). Another possibility is Fourier signal processing. For example, an FFT (Fast Fourier Transform) of the multiplexer output signal can be performed to measure the amplitude (or amplitude and phase) of various spectral components. Signal averaging can be performed in signal processor 630 to improve signal to noise ratio. Such averaging is especially effective when signal detection is phase synchronized. Such synchronization is straightforward, since the magnetic field modulation signal and mixer frequency shift input signals are both available for synchronization purposes. More than 30 dB of noise reduction has been observed by averaging in this manner. Signal processor 630 can perform analog and/or digital processing. In a preferred embodiment, TDM multiplexer 610 includes an analog to digital converter (ADC) at its output, so that signals sent off-chip are digital signals. Typically a high precision ADC is preferred. In the example of FIG. 8, a 16 bit ADC was employed.

Figure 7:
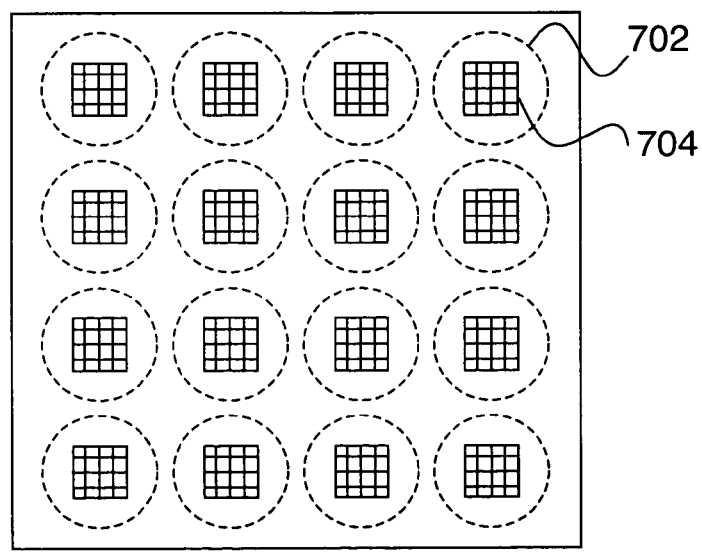
FIG. 7 shows a top view of a sensor array including sensor subarrays according to an embodiment of the invention.

FIG. 7 shows a top view of a sensor array including sensor subarrays according to an embodiment of the invention. As indicated above, sensor elements such as 102 on FIG. 1 can be single sensors or can be subarrays having several sensor pixels. FIG. 7 shows an embodiment having 16 sensor elements, each sensor element being a subarray having several pixels. As indicated in connection with FIG. 2, it is preferred for these pixels to be row and column addressable in a manner similar to conventional semiconductor memory chips.

It is also preferred, but not required, for the subarray size to be comparable to the oligomer probe spot size. On FIG. 7, one of the subarrays is shown as 704, with a corresponding oligomer probe spot 702. Spot 702 and subarray 704 preferably have sizes suitable for the intended application. For example, in biological testing a common probe spot size is a 200 μm circle. In this case, subarray 704 should fit within the 200 μm circle. Larger or smaller probe spot sizes than 200 μm can be employed, and the corresponding preferred subarray size increases or decreases accordingly. In embodiments of the invention having multiple subarrays, each corresponding to an oligomer probe spot, the oligomer probe spots can have the same biological probes or can have different biological probes.

Operation of the embodiment of FIG. 7 can proceed via the following steps. In a first step, a probe coating is deposited on each subarray (e.g., as a liquid drop from a robotic dispenser). In a second step, the probe coating is dried and/or otherwise processed to form probe spots such as 702 on FIG. 7. After completion of this step, the sensors in the subarrays are sensitized to target molecules in the sample that are complimentary to probe molecule in the probe coating. Such selective sensitization is referred to as functionalization. In a third step, sample(s) to be assayed for the presence of tagged target molecules can be delivered to the subarrays via a sample flow arrangement, or can be directly deposited on the probe spots. In a fourth step, binding of target molecules to probe molecules at the subarray sensors elements is detected based on the presence of the magnetic tag.

The active area of the subarrays is less than the physical area of the subarrays, since the sensitive MR devices do not cover the entire subarray area. If a tagged target molecule is bound far away from an MR device, it will not be effectively sensed. Therefore, it is preferred to functionalize the MR device surfaces such that probes bind to the MR device surfaces (i.e. active areas) but not to interstitial areas between the MR devices. Such selective functionalization is described in detail in U.S. patent application Ser. No. 10/829,505 entitled "Magnetic Nanoparticles, Magnetic Detector Arrays, and Methods for their Use in Detecting Biological Molecules".

Thus FIG. 7 shows an embodiment of the invention having several sensor element pixels for each probe spot. Multiplexing methods of the invention are employed to reduce readout time compared to a straightforward sequential readout of all sensor element pixels. For example, each row of subarrays on FIG. 7 can be combined by 4:1 FDM (as shown on FIG. 1), and each column of subarrays on FIG. 7 can be combined by 4:1 TDM (as shown on FIG. 6). The net effect is a 16:1 multiplexing of the subarray outputs. Any other pattern of multiplexing the subarrays is also suitable for practicing the invention. The addressing of pixels within the subarrays is independent of this 16:1 multiplexing. Such multiplexing of sensor subarray outputs dramatically reduces the total readout time compared to subarrays not having multiplexed outputs. This reduced readout time is a key advantage of the invention, enabling high speed and sensitive sensing of tagged sample components.

More specifically, the sensor subarray pixels can be made small enough to detect a single magnetic tag. Since the time for a tagged species to bond to a sensor surface depends mainly on the subarray size, bonding will be rapid for subarrays comparable to the probe spot size. Readout time is reduced by FDM and optionally TDM multiplexing. This high sensitivity makes a microarray assay without a polymerase chain reaction step realizable by the present invention. Conventional assay techniques with less sensitive detection require many magnetic tags (often as many as tens of thousands) to bind to a sensor for detection. Such assays often require costly and laborious biological amplification steps (such as a polymerase chain reaction step) in order to provide a large enough number of bound tags to be sensed.

FIG. 8 shows a chip layout of an embodiment of the invention. The example of FIG. 8 has 16 subarrays (as shown on FIG. 7). The subarrays are separated into four clusters 802, 804, 806, and 808. Each subarray has 64 active sensors in an 8×8 array and 8 reference sensors. It is often convenient, as in this case, to have one reference sensor per row (or column) of active sensors, instead of one reference sensor per active sensor (as on FIG. 2). The active sensors in each subarray are row and column addressable as described above. To reduce noise, 2T1SV sensor cells are employed, as shown on FIG. 4a. The four subarray outputs of cluster 802 are combined by FDM as shown on FIG. 1. Similar combining occurs for clusters 804, 806, and 808. Although the frequency shifts must be distinct within a cluster, frequencies can be reused from cluster to cluster. Thus all four clusters in this example can use the same set of frequencies f1, f2, f3, and f4 for FDM combining. The outputs of clusters 802, 804, 806, and 808 are combined by TDM, as shown on FIG. 6.

The preceding description has been by way of example, as opposed to limitation. In particular, variations of the number of sensor elements, their arrangement, and the physical size and/or separation of the sensor elements are all within the scope of the invention. Examples were given of 4:1 FDM and 4:1 TDM. The invention can be practiced with n:1 FDM for any n greater than one, and can be practiced with or without n:1 TDM for any n greater than one.

The invention claimed is:

1. A sensor for sensing a magnetically tagged sample, the sensor comprising:
   a) two or more sensor subassemblies, each sensor subassembly including:
      i) a magnetoresistive (MR) sensor element providing an analog sensor element signal responsive to the sample; and
      ii) an analog mixer receiving the analog sensor element signal and providing an analog frequency shifted sensor element signal;
   wherein each of the analog mixers provides a distinct frequency shift; and
   b) an output summing junction providing a combined output signal proportional to a sum of the analog frequency shifted sensor element signals.

2. The sensor of claim 1, wherein said sample comprises a biological sample selected from the group consisting of oligomer samples, DNA samples, RNA samples, proteins, peptides, antibodies, antigens, lipids, and viruses.

3. The sensor of claim 1, wherein said sample comprises a chemical sample selected from the group consisting of polymers, toxins, pharmaceutical compounds, biohazardous compounds and explosive compounds.

4. The sensor of claim 1, wherein said sensor is fabricated in part with BiCMOS technology.

5. The sensor of claim 1,
   wherein each of said MR sensor elements includes an MR device, a first transistor and a second transistor,
   wherein the second transistor is connected to the MR device,
   wherein the first transistor has a source-follower relation to the second transistor and provides said analog sensor element signal.

6. The sensor of claim 5, wherein each of said MR sensor elements does not include any transistors other than said first transistor and said second transistor.

7. The sensor of claim 1, wherein each of said MR sensor elements comprises a voltage controlled current source providing current to an MR device.

8. The sensor of claim 1, wherein each of said MR sensor elements comprises a subarray of MR sensor element pixels addressable by a row decoder and a column decoder.

9. The sensor of claim 1, wherein each of said analog mixers comprises a double-balanced, passive CMOS mixer.

10. The sensor of claim 1, wherein each of said subassemblies further includes an amplifier receiving said analog frequency shifted sensor element signal and providing an amplified analog sensor element signal to said summing junction.

11. The sensor of claim 1, wherein each of said subassemblies further includes a reference MR sensor element providing a reference signal received by said analog mixer, and wherein each of said analog mixers provides an output responsive to a difference of its two inputs.

12. The sensor of claim 1, further comprising a signal processor receiving said combined output signal.

13. The sensor of claim 12, wherein phase-sensitive detection of said analog frequency shifted sensor element signals within said combined output signal is performed by said signal processor.

14. The sensor of claim 1, wherein each of said sensor subassemblies further comprises a molecular probe coating on said magnetoresistive sensor element.

15. The sensor of claim 14, wherein each of said molecular probe coatings binds to the same molecular species.

16. The sensor of claim 14, wherein said molecular probe coatings bind to two or more different molecular species.

17. The sensor of claim 14, wherein said molecular probe coatings are only present on active areas of said magnetoresistive sensor elements.

18. A sensor array comprising:
two or more of the sensors of claim 1;
a multiplexer receiving each of said combined output signals and providing a multiplexer output signal;
wherein the multiplexer output signal is related to said combined output signals by time-division multiplexing.

19. The sensor of claim 18, wherein each of said MR sensor elements comprises a subarray of MR sensor element pixels addressable by a row decoder and a column decoder.

20. A method for sensing a magnetically tagged sample, the method comprising:

a) providing two or more sensor subassemblies, each sensor subassembly including:
  i) a magnetoresistive (MR) sensor element providing an analog sensor element signal responsive to the sample; and
  ii) an analog mixer receiving the analog sensor element signal and providing an analog frequency shifted sensor element signal;
wherein each of the analog mixers provides a distinct frequency shift; and
b) providing a combined output signal proportional to a sum of the analog frequency shifted sensor element signals.

21. The method of claim 20, further comprising applying an external magnetic field to said magnetically tagged sample.

22. The method of claim 21, wherein said external magnetic field is modulated at a modulation frequency $f_B$, whereby each of said analog sensor element signals is modulated at $f_B$.

23. The method of claim 20, wherein said MR sensor elements are driven by an electrical signal modulated at a modulation frequency $f_A$, whereby each of said analog sensor element signals is modulated at $f_A$.

* * * * *

UNITED STATES PATENT AND TRADEMARK OFFICE
CERTIFICATE OF CORRECTION

| | | |
|---|---|---|
| PATENT NO. | : 7,939,338 B2 | Page 1 of 1 |
| APPLICATION NO. | : 11/128105 | |
| DATED | : May 10, 2011 | |
| INVENTOR(S) | : Shan X. Wang | |

It is certified that error appears in the above-identified patent and that said Letters Patent is hereby corrected as shown below:

In the Specification

Replace lines 16-18 of column 1 with the following text:

This invention was made with Government support under contract N00014-02-1-0807 awarded by the Department of the Navy ONR. The Government has certain rights in the invention.

Signed and Sealed this
Eighteenth Day of August, 2015

Michelle K. Lee
*Director of the United States Patent and Trademark Office*